(12) United States Patent
O'Brien et al.

(10) Patent No.: US 7,241,835 B2
(45) Date of Patent: *Jul. 10, 2007

(54) COSMETIC COMPOSITIONS COMPRISING SILICONE GELS

(75) Inventors: Michael Joseph O'Brien, Clifton Park, NY (US); Suresh K. Rajaraman, Troy, NY (US)

(73) Assignee: General Electric Company, Schenectady, NY (US)

( * ) Notice: Subject to any disclaimer, the term of this patent is extended or adjusted under 35 U.S.C. 154(b) by 341 days.

This patent is subject to a terminal disclaimer.

(21) Appl. No.: 10/439,857

(22) Filed: May 16, 2003

(65) Prior Publication Data

US 2003/0203979 A1    Oct. 30, 2003

Related U.S. Application Data

(63) Continuation-in-part of application No. 10/393,858, filed on Mar. 21, 2003, now Pat. No. 6,759,479, which is a continuation-in-part of application No. 09/858,795, filed on May 16, 2001, now Pat. No. 6,538,061.

(51) Int. Cl.
   *C08L 83/04* (2006.01)

(52) U.S. Cl. ............... 524/862; 525/577; 525/578; 525/579; 528/15; 528/25; 528/31; 528/32; 524/268; 524/311; 524/315; 524/318; 524/322; 524/379; 524/386; 524/860; 524/861; 524/588; 424/401

(58) Field of Classification Search ........ 524/858–862; 528/31, 32
   See application file for complete search history.

(56) References Cited

U.S. PATENT DOCUMENTS

| | | | |
|---|---|---|---|
| 4,987,169 A | 1/1991 | Kuwata et al. | |
| 5,128,431 A | 7/1992 | Riding et al. | |
| 5,266,321 A * | 11/1993 | Shukuzaki et al. | 424/401 |
| 5,310,843 A * | 5/1994 | Morita | 528/15 |
| 5,354,796 A | 10/1994 | Creecy et al. | |
| 5,493,041 A | 2/1996 | Biggs et al. | |
| 5,663,752 A | 9/1997 | Imamura et al. | |
| 5,698,654 A | 12/1997 | Nye et al. | |
| 5,753,751 A | 5/1998 | Liao et al. | |
| 5,760,116 A * | 6/1998 | Kilgour et al. | 524/268 |
| 5,866,261 A * | 2/1999 | Kerr et al. | 428/447 |
| 5,929,164 A | 7/1999 | Zhang | |
| 5,965,683 A | 10/1999 | Nye et al. | |
| 5,977,280 A | 11/1999 | Kadlec et al. | |
| 6,013,247 A * | 1/2000 | Bara et al. | 424/59 |
| 6,027,738 A * | 2/2000 | Stepniewski et al. | 424/401 |
| 6,046,156 A | 4/2000 | Perry | |
| 6,054,547 A | 4/2000 | Perry et al. | |
| 6,060,546 A | 5/2000 | Powell et al. | |
| 6,075,111 A | 6/2000 | Perry et al. | |
| 6,077,923 A | 6/2000 | Perry et al. | |
| 6,083,901 A | 7/2000 | Perry et al. | |
| 6,153,578 A | 11/2000 | Perry | |
| 6,168,782 B1 | 1/2001 | Lin et al. | 424/78.03 |
| 6,207,717 B1 | 3/2001 | Lin et al. | 514/772.1 |
| 6,262,170 B1 * | 7/2001 | Kilgour et al. | 524/731 |
| 6,271,295 B1 | 8/2001 | Powell et al. | |
| 6,355,724 B1 * | 3/2002 | LeGrow et al. | 524/731 |
| 6,365,696 B1 * | 4/2002 | Westmeyer et al. | 528/12 |
| 6,387,405 B1 * | 5/2002 | Shah et al. | 424/486 |
| 6,423,322 B1 * | 7/2002 | Fry | 424/401 |
| 6,475,500 B2 * | 11/2002 | Vatter et al. | 424/401 |
| 6,479,686 B2 * | 11/2002 | Nakanishi et al. | 556/440 |
| 6,774,179 B2 | 8/2004 | Ferritto et al. | 524/860 |
| 2003/0190336 A1* | 10/2003 | Adams et al. | 424/401 |

FOREIGN PATENT DOCUMENTS

| | | |
|---|---|---|
| EP | 295886 A2 * | 12/1988 |
| EP | 545 002 A1 | 6/1993 |
| WO | WO 98/00103 | 1/1998 |
| WO | WO 98/00104 | 1/1998 |
| WO | WO 98/00105 | 1/1998 |
| WO | WO 98/04236 | 2/1998 |
| WO | WO 98/18438 | 5/1998 |
| WO | WO 00/08087 | 2/2000 |

OTHER PUBLICATIONS

"A Consumer's Directory of Cosmetic Ingredients" Ruth Winter, Crown Trade Paperbacks, 1994.*
U.S. Appl. No. 10/922,487, commonly assigned.*
U.S. Appl. No. 10/719,154, commonly assigned.*
U.S. Appl. No. 10/100,637, filed Mar. 18, 2002, Michael J. O'Brien et al.

* cited by examiner

*Primary Examiner*—Marc S. Zimmer
(74) *Attorney, Agent, or Firm*—Kenneth S. Wheelock

(57) ABSTRACT

Methods for making homogenized cosmetic formulations comprising a silicone gel.

26 Claims, No Drawings

COSMETIC COMPOSITIONS COMPRISING SILICONE GELS

CROSS-REFERENCE TO RELATED APPLICATIONS

The instant application is a Continuation-In-Part application of U.S. Ser. No. 10/393,858 filed Mar. 21, 2003 now U.S. Pat. No. 6,759,479 which is a Continuation-In-Part application of U.S. Ser. No. 09/858,795 filed May 16, 2001 now U.S. Pat. No. 6,538,061.

FIELD OF THE INVENTION

The present invention relates to methods of making cosmetic compositions comprising silicone polymer networks comprising personal care ingredients and methods for making such silicone compositions.

BACKGROUND OF THE INVENTION

The personal care industry thrives on being able to deliver multiple performance products based on mixtures of several components, with each having performance characteristics important to or desirable in the final formulation. One desirable characteristic is the ability to provide a silky initial feel derived from low molecular weight silicones, such as for example, octamethylcyclotetrasilioxane or decamethylcyclopentasiloxane, in the formulation while maintaining a high, but shear-thinnable viscosity. While these low molecular weight silicones provide the desired feel characteristics, they are also low viscosity, highly flowable liquids. Thus they are not easily held in a formulation, preferring rather to separate and flow out of a given container or flow uncontrollably across the skin when used in a specific application. Further, it desirable to achieve an initial silky feel while providing a smooth, low-residue feel upon dry-down. Polymeric silicone gels prepared in volatile silicone have been found to deliver desirable initial feel of volatile, low viscosity silicones to formulations while at the same time provide high viscosity and a smooth silky feel on dry-down, see for example, U.S. Pat. Nos. 5,760,116, 5,493,041 and 4,987,169.

SUMMARY OF THE INVENTION

The present invention provides for a method of making a cosmetic composition comprising:
(a) preparing a silicone gel; and (b) dispersing the silicone gel in a dispersant medium; optionally followed by homogenizing the gel and optionally adding personal care ingredients or optionally adding personal care ingredients followed by an optional homogenization. More particularly the present invention provides for a method of making a cosmetic composition wherein the silicone gel is selected from the group of gels consisting of:
(i) a gel formed from a silicone and a hydrosilylation compatible solvent wherein said silicone is prepared by the hydrosilylation of a linear alkenyl polyorganosiloxane and a hydride resin;
(ii) a gel formed as a reaction product of an epoxy functional hydrido-siloxane said reaction product being formed in an epoxy-gel formation compatible solvent;
(iii) a gel formed from a silicone and a hydrosilylation compatible solvent wherein said silicone is prepared by the hydrosilylation of a linear hydrogen polyorganosiloxane and an alkenyl resin;
(iv) a gel formed from a silicone and a hydrosilylation compatible solvent wherein said silicone is prepared by the hydrosilylation of a linear hydrogen polyorganosiloxane and a linear alkenyl polyorganosiloxane;
(v) a gel formed from a silicone and a hydrosilylation compatible solvent wherein said silicone is prepared by the hydrosilylation of a hydrogen polyorganosiloxane resin and an alkenyl polyorganosiloxane resin;
(vi) a gel formed from a silicone and a hydrosilylation compatible solvent wherein said silicone is prepared by the hydrosilylation of a linear hydrogen organopolysiloxane having two or more hydride functionalities per molecule and an $\alpha, \omega$ reactive organic molecule possessing two or more reactive functionalities per molecule; and
(vii) a gel formed as a reaction product of a vinyl functional hydrido-siloxane in a hydrosilylation compatible solvent.

This present invention provides for a method for preparation of cosmetic compositions comprising swollen cross-linked silicone network compositions. The present invention also provides for cosmetic compositions comprising colored materials or pigments.

DETAILED DESCRIPTION OF THE INVENTION

Applicants have discovered that improved cosmetic formulations are obtained using silicone gels. These silicone gels may be prepared by a variety of synthetic routes. The cosmetic formulations of the present invention are all prepared by a variety of methods that incorporate homogenization or particle size reduction at one or more steps in the method of preparation. The preparation of the gels and their subsequent homogenization afford a convenient method of incorporating additional materials, so-called personal care ingredients (later defined) or active ingredients. The preferred methods of making the cosmetic compositions of the present invention involve: 1) the preparation of the silicone gel and addition or incorporation of personal care ingredients or active ingredients prior to homogenization or particle size reduction or 2) preparation of the silicone gel in the presence of personal care ingredients or active ingredients followed by homogenization.

As used herein the phrase "silicone gel" refers to any silicone containing material that increases its volume upon contact with a low molecular weight solvent that may or may not be volatile wherein the solvent diffuses into the silicone containing material.

As used herein the terms polyorganosiloxane and organopolysiloxane are interchangeable one with the other.

As used herein the term "colored material" refers to physiologically acceptable dyes, pigments or other coloring material known to the cosmetic arts. The term "physiologically acceptable" is an accepted term of art and refers to topical application on humans.

As used herein the phrase "silicone containing material" refers to oligomers, polymers, copolymers, terpolymers and higher order polymers of silicon containing repeat units, copolymers and higher order interpolymers containing silicon repeat units with organic polymers. As used herein "organic polymers" means organic polymers wherein the repeat units do not contain silicon atoms in the polymeric backbone or chain. Thus for example, some silicones gels useful in the compositions of the present invention are polymeric, cross-linked, networks of organopolysiloxanes or block copolymers of organopolysiloxanes and organic polymers. The cross-linking of either type of network may be achieved by cross-linking units based on siloxanes comprising hydrido-, vinyl-, epoxy-, acrylate-, acetoxy-, or alkoxy-groups and the like and mixtures thereof and when such materials contain organic polymers as a component, organic compounds or oligomers capable of joining polymeric units together, e.g. terminal polyolefins, terminal polyolefinic ethers, acrylates, epoxides and the like and blends thereof. Silicone gels useful in the compositions of the present invention are exemplified in the following U.S. Pat. Nos. 4,987,169; 4,980,167; 5,760,116; 5,811,487 and 5,138,009 hereby and herewith specifically incorporated by reference.

As used herein the phrase "low molecular weight volatile solvent" refers to any solvent compatible with topical application to human beings without adverse effect thereto that has a vapor pressure between the temperatures of 0° C. and 100° C. ranging from about 1 mm Hg to 760 mm Hg.

As used herein the phrase one to eighty carbon atom monovalent hydrocarbon radical means a monovalent radical having from one to eighty carbon atoms and optionally from zero to eighty hetero atoms selected from the group consisting of oxygen, nitrogen, and sulfur.

The silicone gels utilized in the formulations enabled by the present invention may be prepared in a variety of chemically appropriate solvents (hereinafter defined and listed). Once prepared, the silicone gels may be dispersed in a variety of chemically appropriate solvents (hereinafter defined and listed).

While a variety of silicone gels may be prepared by condensation cure mechanisms, e.g. room temperature vulcanizable compositions, the following specific silicone gels are preferred.

Silicone Gel I.

The present invention may utilize a silicone gel composition comprising:

(A) a first silicone formed by the hydrosilylation product of (1) a linear alkenyl polyorganosiloxane having the formula:

$$M^{vi}_a D_x D^{vi}_y M_{2-a}$$

where the subscript x is a number greater than 10, the subscript y is a number ranging from zero to about 20, the subscript a is a number ranging from 0 to 2, subject to the limitation that a+y is within the range of from 1 to about 20, with $M^{vi}$ defined as:

$$R^1 R^2 R^3 SiO_{1/2}$$

where $R^1$ is a monovalent unsaturated hydrocarbon radical having from two to ten carbon atoms, and $R^2$ and $R^3$ are each independently one to eighty carbon atom monovalent hydrocarbon radicals, with D defined as:

$$R^4 R^5 SiO_{2/2}$$

where $R^4$ and $R^5$ are each independently one to eighty carbon atom monovalent hydrocarbon radicals, with $D^{vi}$ defined as:

$$D^{vi} = R^6 R^7 SiO_{2/2}$$

where $R^6$ is a monovalent unsaturated hydrocarbon radical having from two to ten carbon atoms, and $R^7$ is independently a one to eighty carbon atom monovalent hydrocarbon radical with M defined as $$M = R^8 R^9 R^{10} SiO_{1/2}$$

with $R^8$, $R^9$, and $R^{10}$ each independently a one to eighty carbon atom monovalent hydrocarbon radical; and (2) a hydride resin having the formula:

$$(M^H_w Q_z)_j$$

where Q has the formula $SiO_{4/2}$ and with $M^H$ defined as $$H_b R^{11}_{3-b} SiO_{1/2}$$

where $R^{11}$ is a one to eighty carbon atom monovalent hydrocarbon radical where the subscript b is a number ranging from 1 to 3, with the subscripts w and z having a ratio of 0.5 to 4.0 respectively and the subscript j ranges from about 2.0 to about 100; wherein said hydrosilylation is conducted in the presence of (3) a hydrosilylation compatible solvent preferably a silicone having a viscosity below about 1,000 centistokes at 25° C. or a hydrosilylation compatible lipohilic phase (hereinafter also referred to as a hydrosilylation compatible solvent), thereby forming a gel; and (B) a lipophilic phase or a silicone having a viscosity below about 1,000 centistokes at 25° C. (hereinafter also referred to as dispersant medium or media) wherein said hydrosilylation product is slurried in said lipophilic phase or said silicone and subjected to mixing with said lipophilic phase or said silicone; producing thereby a uniform mixture comprising said lipophilic phase or said silicone and said hydrosilylation product whereby said uniform mixture has a viscosity ranging from 500 to 500,000 centistokes at 25° C.

The silicone having a viscosity below about 1,000 centistokes at 25° C. is preferably selected from the group consisting of cyclic silicones having the formula:

$$D_f$$

where the subscript f is an integer ranging from about three to about 6 with D defined as:

$$R^4 R^5 SiO_{2/2}$$

where $R^4$ and $R^5$ are each independently one to eighty carbon atom monovalent hydrocarbon radicals, the group of linear silicones having the formula:

$$M'D'_j M'$$

where D' is defined as:

$$R^4 R^5 SiO_{2/2}$$

where $R^4$ and $R^5$ are each independently one to eighty carbon atom monovalent hydrocarbon radicals and M' has the formula:

$$R^{12} R^{13} R^{14} SiO_{1/2}$$

where $R^{12}$, $R^{13}$ and $R^{14}$ are each independently one to eighty carbon atom monovalent hydrocarbon radicals and the group of branched silicones having the formula:

$$T_{N'} D'_{N'} M'_{N''}$$

where D' and M' are each independently selected and are as previously defined and $T=R^{2'}SiO_{3/2}$, where $R^{2'}$ is independently selected and is as previously defined and the subscript אּ' is at least 1, the subscript אּ" ranges from 0 to 3 אּ' and the subscript אּ is 0 or positive with all three subscripts chosen so that the viscosity of $T_{אּ}D'_{אּ}M'_{אּ"}$ is 1,000 centipose or less at 25° C.

Silicone Gel II.

Other gels suitable for the compositions of the present invention comprise the reaction products of an epoxy functional hydrido-siloxane molecule having the following formula:

$$M_\alpha M^H_\beta M^E_\chi D_\delta D^H_\epsilon D^E_\phi T_\gamma T^H_\eta T^E_\iota Q_\kappa$$

where
$M=R^{1'}R^{2'}R^{3'}SiO_{1/2}$;
$M^H=R^{4'}R^{5'}HSiO_{1/2}$;
$M^E=R^{6'}R^{7'}R^ESiO_{1/2}$;
$D=R^{8'}R^{9'}SiO_{2/2}$;
$D^H=R^{10'}HSiO_{2/2}$;
$D^E=R^{11'}R^ESiO_{2/2}$;
$T=R^{12'}SiO_{3/2}$;
$T^H=HSiO_{3/2}$;
$T^E=R^ESiO_{3/2}$; and
$Q=SiO_{4/2}$;

where $R^{1'}$, $R^{2'}$, $R^{3'}$, $R^{8'}$, $R^{9'}$ and $R^{12'}$ are independently monovalent hydrocarbon radicals having from one to sixty carbon atoms; $R^{4'}$, $R^{5'}$ and $R^{10'}$ are independently monovalent hydrocarbon radicals having from one to sixty carbon atoms or hydrogen; $R^{6'}$, $R^{7'}$, $R^{11'}$ are independently monovalent hydrocarbon radicals having from one to sixty carbon atoms or $R^E$; each $R^E$ is independently a monovalent hydrocarbon radical containing one or more oxirane moieties having from one to sixty carbon atoms; the stoichiometric subscripts $\alpha$, $\beta$, $\chi$, $\delta$, $\epsilon$, $\phi$, $\gamma$, $\eta$, $\iota$, and $\kappa$ are either zero or positive subject to the following limitations: $\alpha+\beta+\chi>1$; $\beta+\epsilon+\eta>1$; $\chi+\phi+\iota>1$; $\beta+\epsilon+\eta>\chi+\phi+\iota$; and when $\delta+\epsilon+\phi+\gamma+\eta+\iota+\kappa=0$, $\alpha+\beta+\chi=2$.

The reaction product of an epoxy functional hydrido siloxane molecule is preferably prepared in an epoxy gel formation medium selected from a lipophilic phase or a silicone fluid selected from the group consisting of cyclic silicones having the formula:

$$D_f$$

where the subscript f is an integer ranging from about three to about 6 with D defined as:

$$R^4R^5SiO_{2/2}$$

where $R^4$ and $R^5$ are each independently one to eighty carbon atom monovalent hydrocarbon radicals, the group of linear silicones having the formula:

$$M'D'_iM'$$

where D' is defined as:

$$R^4R^5SiO_{2/2}$$

where $R^4$ and $R^5$ are each independently one to eighty carbon atom monovalent hydrocarbon radicals and M' has the formula:

$$R^{12}R^{13}R^{14}SiO_{1/2}$$

where $R^{12}$, $R^{13}$ and $R^{14}$ are each independently one to eighty carbon atom monovalent hydrocarbon radicals and the group of branched silicones having the formula:

$$T_{אּ'}D'_{אּ}M'_{אּ"}$$

where D' and M' are each independently selected and are as previously defined and $T=R^{2'}SiO_{3/2}$, where $R^{2'}$ is independently selected and is as previously defined and the subscript אּ' is at least 1, the subscript אּ" ranges from 0 to 3 אּ' and the subscript אּ is 0 or positive with all three subscripts chosen so that the viscosity of $T_{אּ'}D'_{אּ}M'_{אּ"}$ is 1,000 centipose or less at 25° C.

Once prepared, the type II silicone gels that may be utilized in the composition of the present invention may be slurried and mixed in a dispersant medium selected from a lipophilic phase or a silicone selected from the group consisting of cyclic silicones having the formula $$D_f$$

where the subscript f is an integer ranging from about three to about 6 with D defined as:

$$R^4R^5SiO_{2/2}$$

where $R^4$ and $R^5$ are each independently one to eighty carbon atom monovalent hydrocarbon radicals, the group of linear silicones having the formula:

$$M'D'_iM'$$

where D' is defined as:

$$R^4R^5\ SiO_{2/2}$$

where $R^4$ and $R^5$ are each independently one to eighty carbon atom monovalent hydrocarbon radicals and M' has the formula:

$$R^{12}R^{13}R^{14}SiO_{1/2}$$

where $R^{12}$, $R^{13}$ and $R^{14}$ are each independently one to eighty carbon atom monovalent hydrocarbon radicals and the group of branched silicones having the formula:

$$T_{אּ'}D'_{אּ}M'_{אּ"}$$

where D' and M' are each independently selected and are as previously defined and $T=R^{2'}SiO_{3/2}$, where $R^{2'}$ is independently selected and is as previously defined and the subscript אּ' is at least 1, the subscript אּ" ranges from 0 to 3 אּ' and the subscript אּ is 0 or positive with all three subscripts chosen so that the viscosity of $T_{אּ'}D'_{אּ}M'_{אּ"}$ is 1,000 centipose or less at 25° C.

Silicone Gel III.

The present invention may utilize a silicone gel composition comprising:

(A) a silicone formed by the hydrosilylation product of
  (1) a linear hydrogen polyorganosiloxane having the formula:

$$M^H_aD_xD^H_yM_{2-a}$$

where the subscript x is a number greater than 10, the subscript y is a number ranging from zero to about 20, the subscript a is a number ranging from 0 to 2, subject to the limitation that a+y is within the range of from 1 to about 20, with $M^H$ defined as:

$$R^1R^2R^3SiO_{1/2}$$

where $R^1$ is hydrogen, $R^2$ and $R^3$ are each independently one to eighty carbon atom monovalent hydrocarbon radicals, with D defined as:

$$R^4R^5SiO_{2/2}$$

where $R^4$ and $R^5$ are each independently one to eighty carbon atom monovalent hydrocarbon radicals, with $D^H$ defined as:

$$D^H=R^6R^7SiO_{2/2}$$

where $R^6$ is hydrogen and $R^7$ is independently a one to eighty carbon atom monovalent hydrocarbon radical with M defined as $$M=R^8R^9R^{10}SiO_{1/2}$$

with $R^8$, $R^9$, and $R^{10}$ each independently a one to eighty carbon atom monovalent hydrocarbon radical; and (2) an alkenyl resin having the formula:

$$(M^{vi}{}_wQ_z)_j$$

where Q has the formula $SiO_{4/2}$ and with $M^{vi}$ defined as $$R^{11}{}_bR^{12}{}_{3-b}SiO_{1/2}$$

where $R^{11}$ is a monovalent unsaturated hydrocarbon radical having from two to ten carbon atoms, $R^{12}$ is a one to eighty carbon atom monovalent hydrocarbon radical where the subscript b is a number ranging from 1 to 3, with the subscripts w and z having a ratio of 0.5 to 4.0 respectively and the subscript j ranges from about 2.0 to about 100; wherein said hydrosilylation is conducted in the presence of (3) a hydrosilylation compatible solvent preferably a silicone having a viscosity below about 1,000 centistokes at 25° C. or a hydrosilylation compatible lipohilic phase (hereinafter also referred to as hydrosilylation compatible solvent), thereby forming a gel; and (B) a lipophilic phase or a silicone having a viscosity below about 1,000 centistokes at 25° C. (hereinafter also referred to as dispersant medium or media) wherein said hydrosilylation product is slurried in said lipophilic phase or said silicone and subjected to mixing with said lipophilic phase or said silicone; producing thereby a uniform mixture comprising said lipophilic phase or said silicone and said hydrosilylation product whereby said uniform mixture has a viscosity ranging from 500 to 500,000 centistokes at 25° C.

Silicone Gel IV

A first silicone being the hydrosilylation reaction product of a linear alkenyl organopolysiloxane (as previously defined) having two or more alkenyl functionalities per molecule as above with a linear hydrogen organopolysiloxane (as previously defined) having two or more hydrogen functionalities per molecule prepared as above in the presence of a hydrosilylation compatible solvent or silicone, $D_f$, $M'D'_iM'$ or $T_RD'_RM'_{R''}$ where $D_f$, $M'D'_iM'$ and $T_RD'_RM'_{R''}$ are as previously defined. The gel as prepared may then be slurried with a lipophilic phase or a silicone having a viscosity below about 1,000 centistokes at 25° C. (hereinafter also referred to as dispersant medium or media) wherein said hydrosilylation product is slurried in said lipophilic phase or said silicone and subjected to mixing with said lipophilic phase or said silicone; producing thereby a uniform mixture comprising said lipophilic phase or said silicone and said hydrosilylation product whereby said uniform mixture has a viscosity ranging from 500 to 500,000 centistokes at 25° C.

Silicone Gel V

A first silicone being the hydrosilylation reaction product of an alkenyl organopolysiloxane resin having two or more alkenyl functionalities per molecule having the formula $$M^{vi}{}_cD_dD^{vi}{}_eT_gT^{vi}{}_kM_{2-c}M''{}_{g+k}$$

with a hydrogen organopolysiloxane resin having two or more hydrogen functionalities per molecule having the formula $$M^H{}_nD_pD^H{}_rT_sT^H{}_uM_vM''{}_{s+u}$$

where all the terms are as previously defined with $T=R^{16}SiO_{3/2}$ where $R^{16}$ is a one to eighty carbon atom monovalent hydrocarbon radicals;

$T^{vi}=R^{17}SiO_{3/2}$ where $R^{17}$ is a monovalent unsaturated hydrocarbon radical having from two to forty carbon atoms;

$T^H=HSiO_{3/2}$;

M" is independently $M^H$, $M^{vi}$ or M and the subscripts c, d, e, g, k, n, p, r, s, u, and v are either zero or positive subject to the limitations that g+k+s+u is $\geq 1$; c+e+k$\geq 2$ and n+r+u$\geq 2$; prepared in a hydrosilylation compatible solvent and slurried in a lipophilic phase or a silicone having a viscosity below about 1,000 centistokes at 25° C. (hereinafter also referred to as dispersant medium or media) wherein said hydrosilylation product is slurried in said lipophilic phase or said silicone and subjected to mixing with said lipophilic phase or said silicone; producing thereby a uniform mixture comprising said lipophilic phase or said silicone and said hydrosilylation product whereby said uniform mixture has a viscosity ranging from 500 to 500,000 centistokes at 25° C.

Silicone Gel VI

A first silicone being the reaction product of a linear hydrido organopolysiloxane having two or more hydride functionalities per molecule with an α, ω reactive organic molecule possessing two or more reactive functionalities per molecule in the presence of a lipophilic phase or second silicone, $D_f$, $M'D'_iM'$ or $T_RD'_RM'_{R''}$ where $D_f$, $M'D'_iM'$ and $T_RD'_RM'_{R''}$ are as previously defined. The reactive functionalities of the α, ω reactive organic molecule possessing two or more functionalities per molecule are selected from the group of organic functional groups consisting of olefins, acetylenes, vinylethers, acrylates or acrylate esters (eg CH2=CHCOOROCOCH=CH2), and alcohols and the like. Thus the α, ω reactive organic molecule possessing two or more functionalities per molecule subtends a large group of organic molecules that includes α, ω-di-olefins, α, ω-olefins possessing a polyolefinic functionality, α, ω-di-acetylenes, α, ω-di-acetylenes possessing a polyacetylenic functionality, including side chain substituted variations where the side chains possess reactive functionality as herein defined. This gel is prepared in a hydrosilylation compatible solvent and slurried in a lipophilic phase or a silicone having a viscosity below about 1,000 centistokes at 25° C. (hereinafter also referred to as dispersant medium or media) wherein said hydrosilylation product is slurried in said lipophilic phase or said silicone and subjected to mixing with said lipophilic phase or said silicone; producing thereby a uniform mixture comprising said lipophilic phase or said silicone and said hydrosilylation product whereby said uniform mixture has a viscosity ranging from 500 to 500,000 centistokes at 25° C.

Silicone Gel VII

Other gels suitable for the compositions of the present invention comprise the reaction products of a vinyl functional hydrido-siloxane molecule having the following formula:

$$M_aM^{vi}{}_bM^H{}_cD_{d'}D^{vi}{}_eD^H{}_fT_{g'}T^{vi}{}_{h'}T^H{}_iQ_{j'}$$

where all the terms are as previously defined and the subscripts a', b', c', d', e', f', g', h', i' and j' are either 0 or a positive integer for well defined molecular species subject to the limitation b'+e'+h' is greater than or equal to one and further subject to the limitation that c'+f'+i' is greater than or equal to one. Mixtures of compounds where individual molecular species possess the formula, $M_aM^{vi}{}_bM^H{}_cD_{d'}D^{vi}{}_eD^H{}_fT_{g'}T^{vi}{}_{h'}T^H{}_iQ_{j'}$, will analyze for non-integral values of the subscripts because of the fact that it is a mixture and not a pure compound. Thus for mixtures of compounds possessing the formula, $M_aM^{vi}{}_bM^H{}_cD_{d'}D^{vi}{}_eD^H{}_fT_{g'}T^{vi}{}_{h'}T^H{}_iQ_{j'}$, the subscripts a', b', c', d', e', f', g', h', i' and j' will be zero or positive. Compounds possessing the formula $M_aM^{vi}{}_bM^H{}_cD_{d'}D^{vi}{}_eD^H{}_fT_{g'}T^{vi}{}_{h'}T^H{}_{i'}Q_{j'}$ may be prepared by the procedures and methods disclosed in U.S. Pat. Nos. 5,698,654; 5,753,751; and 5,965,683 herewith specifically incorporated by reference. These materials may be reacted with the silicone precursors to the class II silicone gels previously defined herein or they may self-reacted in the presence of a noble metal hydrosilylation catalyst as is known in the art. These materials are prepared in a hydrosilyation compatible solvent and slurried in a lipophilic phase or a silicone having a viscosity below about 1,000 centistokes at 25° C. (hereinafter also referred to as dispersant medium or media) wherein said hydrosilylation product is slurried in said lipophilic phase or said silicone and subjected to mixing with said lipophilic phase or said silicone; producing thereby a uniform mixture comprising said lipophilic phase or said silicone and said hydrosilylation product whereby said uniform mixture has a viscosity ranging from 500 to 500,000 centistokes at 25° C.

Many types of noble metal catalysts for hydrosilylation (or SiH olefin addition reaction) are known and such noble metal catalysts may be used for the preparative reactions involved in making the compositions of the present invention. The most preferred noble metals are those of the platinum group metals, specifically rhodium and platinum. When optical clarity of the resulting addition product is required the preferred catalysts are those catalysts that are compounds that are soluble in the reaction mixture. One such platinum compound can be selected from those having the formula (PtCl$_2$Olefin) and H(PtCl$_3$Olefin) as described in U.S. Pat. No. 3,159,601, hereby incorporated by reference. The olefin shown in the previous two catalyst compound formulas can be almost any type of olefin but is preferably an alkenylene having from 2 to 8 carbon atoms, a cycloalkenylene have from 5 to 7 carbon atoms or styrene. Specific olefins utilizable in the above formulas are ethylene, propylene, the various isomers of butylene, octylene, cyclopentene, cyclohexene, cycloheptene, and the like.

A further platinum containing material usable in the compositions of the present invention is the cyclopropane complex of platinum chloride described in U.S. Pat. No. 3,159,662 hereby incorporated by reference.\

Further the platinum containing material can be a complex formed from chloroplatinic acid with up to 2 moles per gram of platinum of a member selected from the class consisting of alcohols, ethers, aldehydes and mixtures of the above as described in U.S. Pat. No. 3,220,972 hereby incorporated by reference.

The catalysts are described in U.S. Pat. Nos. 3,715,334; 3,775,452; and 3,814,730 to Karstedt. Additional background concerning the art may be found at J. L. Spier, "Homogeneous Catalysis of Hydrosilation by Transition Metals, in *Advances in Organometallic Chemistry*, volume 17, pages 407 through 447, F. G. A. Stone and R. West editors, published by the Academic Press (New York, 1979). Persons skilled in the art can easily determine an effective amount of noble metal or platinum catalyst. Generally, an effective amount ranges from about 0.1 to 50 parts per million of the total organopolysiloxane composition.

The cosmetic compositions of the present invention are prepared in general by preparing the gels herein described, dispersing the gels in a dispersing medium and homogenizing the dispersed gels. The addition of pigments, personal care ingredients or active ingredients to the gels and the dispersant medium creates the cosmetic compositions of the present invention. The methods of the present comprise: 1) the addition of pigments, personal care ingredients or active ingredients to the gel precursors and forming the gels in the presence of pigments, personal care ingredients or active ingredients, dispersing the resultant gel in a dispersant medium and homogenizing the gel, the pigments, personal care ingredients or active ingredients, and the dispersant medium; 2) preparing the gel, adding thereto pigments, personal care ingredients or active ingredients either before or after dispersing the gel in a dispersant medium followed by homogenization; and 3) preparing the gel, dispersing it in a dispersant medium, homogenizing the gel in the dispersant medium and adding thereto pigments, personal care ingredients or active ingredients.

The gels of the present invention are prepared either in a hydrosilylation compatible medium or solvent or an epoxygel formation compatible medium or solvent depending on the chemical nature of the gel being prepared. Both classes of preparation media include silicone solvents, preferably a silicone selected from the group of cyclic silicones having the formula $$D_f$$

where the subscript f is an integer ranging from about three to about 6 with D defined as $$R^4R^5SiO_{2/2}$$

where $R^4$ and $R^5$ are each independently one to eighty carbon atom monovalent hydrocarbon radicals; the group of linear silicones having the formula $$M'D'_iM'$$

where D' is defined as $$R^4R^5SiO_{2/2}$$

where $R^4$ and $R^5$ are each independently one to eighty carbon atom monovalent hydrocarbon radicals and M' has the formula $$R^{12}R^{13}R^{14}SiO_{1/2}$$

where $R^{12}$, $R^{13}$ and $R^{14}$ are each independently one to eighty carbon atom monovalent hydrocarbon radicals; and the group of branched silicones having the formula:

$$T_{k'}D'_{k'}M'_{k''}$$

where D' and M' are each independently selected and are as previously defined and $T=R^2SiO_{3/2}$, where $R^2$ is independently selected and is as previously defined and the subscript ℵ' is at least 1, the subscript ℵ" ranges from 0 to 3 ℵ' and the subscript ℵ is 0 or positive with all three subscripts chosen so that the viscosity of $T_ℵD'_ℵM'_{ℵ"}$ is 1,000 centipose or less at 25° C.

The hydrosilylation compatible medium or solvent are selected from the group consisting of silicones and substituted silicones including: silicone oils of the desired viscosity from $D_4$ to 10,000 cps oils; polyethersilicone copolymers where the polyethers vary from 200 to 3000 molecular weight and may consist of alkylene oxide chains based on one, two or more types of monomer units such as ethylene oxide, propylene oxide or butylene oxide and may be attached to the silicone with 1 to six carbon chain, or through an silicone oxygen bond; polyester silicone copolymers; alkyl, aromatic or alkylaromatic substituted siloxanes; alkoxy substituted siloxanes including: substituted methoxy, ethoxy, propoxy, octyloxy, dodecanoxy, cetyryloxy or isostearyloxy siloxanes or other organically substituted siloxanes or siloxanes containing multiple organic substituents that are compatible with hydrosilylation reactions; hydro carbon solvents including: tetradecane, isododecane, isohexadecane, mineral oil, hydrogenate polydecene, apricot oil; ester solvents including: isopropyl myristate, diisopropyl adipate, isodecyl neopentanoate; ethers including: PPG-14 butyl ether, PPG 3 myristyl ether, ethoxylated alkylphenols; glyceryl esters of fatty acids including: sunflower oils, caprylic/capric triglyceride, $C_{10\_}18$ triglyceride; fatty acid glycerides including: glyceryl stearate, glyceryl dioleate; non-volatile fluorinated oil including: fluorinated silicones and fluorinated esters; aromatic solvents including; benzene, toluene and alkylbenzenes; and alcohols including: isopropanol, octanol, dodecanol, hexadecanol, cetearyl alcohol, isostearyl alcohol, myristyl alcohol.

The epoxy gel formation compatible medium or solvent is primarily defined by solvent inertness and is preferably selected from the group of silicone solvents $D_f$, $M'D'_iM'$ or $T_ℵD'_ℵM'_{ℵ"}$ where $D_f$, $M'D'_iM'$ and $T_ℵD'_ℵM'_{ℵ"}$ are as previously defined and hydrocarbon solvents selected from the group consisting of paraffinic, iso-paraffinic, aromatic and alkyl aromatic solvents.

The compositions according to the present invention therefore advantageously comprise a stable dispersion of particles of at least one silicone in a dispersant medium preferably, a lipophilic phase, the lipophilic phase preferably selected from the group consisting of 1) physiologically acceptable liquid lipophilic or fatty phases and 2) silicone fluids selected from the group consisting of $D_f$, $M'D'_iM'$ or $T_ℵD'_ℵM'_{ℵ"}$ where $D_f$, $M'D'D'_iM'$ and $T_ℵD'_ℵM'_{ℵ"}$ are as previously defined.

These dispersions may in particular be provided in the form of nanoparticles of silicone gel in a stable dispersion in the said lipophilic or fatty phase. The nanoparticles are preferably of between 5 and 600 nm in size, given that above about 600 nm the dispersions of particles become much less stable. This size range includes all specific values and subranges therebetween, including 10, 25, 50, 100, 200, 300, 400 and 500 nm.

The liquid lipophilic or fatty phase in which the siloxane or silicone polymer may be dispersed may consist of any cosmetically or dermatologically acceptable, and more generally physiologically acceptable, oil chosen in particular from oils of inorganic, animal, plant or synthetic origin, carbonaceous oils, hydrocarbon oils, fluorinated oils and/or silicone oils, alone or in the form of a mixture insofar as they form a homogeneous and stable mixture and are compatible with the use envisaged. "Liquid fatty phase" refers to any nonaqueous medium which is liquid at room temperature. "Volatile fatty phase" refers to any nonaqueous medium capable of evaporating from the skin or the lips, at room temperature, in less than one hour.

Nonvolatile liquid lipophilic or fatty phase which can be used in the invention, include hydrocarbon oils such as paraffin oil or liquid petroleum jelly, vison oil, turtle oil, soya bean oil, perhydrosqualene, sweet almond oil, calophyllum oil, palm oil, grapeseed oil, sesame oil, maize oil, parleam oil, arara oil, rapeseed oil, sunflower oil, cottonseed oil, apricot oil, castor oil, avocado oil, jojoba oil, olive oil or cereal germ oil; esters of lanolic acid, oleic acid, lauric acid or stearic acid; fatty esters, such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl or linolenyl alcohol, isostearyl alcohol or octyl dodecanol; silicone oils such as polydimethylsiloxane (PDMS), which are optionally phenylated, such as phenyl trimethicones, or which are optionally substituted with optionally fluorinated aliphatic and/or aromatic groups, or with functional groups such as hydroxyl, thiol and/or amine groups; polysiloxanes modified with fatty acids, fatty alcohols or polyoxyalkylenes, fluorinated silicones and perfluorinated oils.

One or more oils which are volatile at room temperature and atmospheric pressure may optionally be used. These volatile oils have for example a steam pressure at ambient temperature and pressure of, preferably, from $1 \times 10^{-3}$ to 300 mm Hg, provided that the boiling point is greater than 25° C. These volatile oils facilitate in particular the application of the composition to the skin, the mucous membranes and the superficial body growths. These oils may be hydrocarbon oils, silicone oils optionally comprising alkyl or alkoxy groups at the end of the silicone or pendant chain.

The volatile silicone oil which may be used in the invention, is selected from the group consisting of $D_f$, $M'D'_iM'$ or $T_ℵD'_ℵM'_{ℵ"}$ where $D_f$, $M'D'_iM'$ and $T_ℵD'_ℵM'_{ℵ"}$ as previously defined. The volatile oils represent preferably from 0 to 97.5% of the total weight of the composition, and more preferably from 5 to 85%. These ranges include all specific values and subranges therebetween, including 0.5, 1, 2, 8, 10, 15, 25, 30, 50, 60, 70, 80, 90 and 95% by weight.

Among the liquid lipophilic or fatty phases suitable for the compositions of the present invention are vegetable oils formed by esters of fatty acids and polyols, in particular triglycerides, such as sunflower, sesame or rapeseed oil, or the esters derived from long-chain acids or alcohols (that is to say having from 6 to 20 carbon atoms), in particular the esters of formula RCOOR' in which R represents the residue of a higher fatty acid containing from 7 to 19 carbon atoms and R'represents a hydrocarbon chain containing from 3 to 20 carbon atoms, such as palmitates, adipates and benzoates, in particular diisopropyl adipate. There may also be mentioned the hydrocarbons and in particular paraffin oils, liquid petroleum jelly, or hydrogenated polyisobutylene, isododecane, or alternatively the "ISOPARs", volatile isoparaffins. There may also be mentioned the silicone oils such as polydimethylsiloxanes and polymethylphenylsiloxanes, optionally substituted with optionally fluorinated aliphatic and/or aromatic groups, or with functional groups such as hydroxyl, thiol and/or amine groups, and the volatile, in particular cyclic, silicone oils. There may also be mentioned the solvents, alone or in the form of a mixture, chosen from (i) linear, branched or cyclic esters having more than 6 carbon atoms, (ii) ethers having more than 6 carbon atoms, (iii) ketones having more than 6 carbon atoms. Monoalcohols having an overall solubility parameter according to the HANSEN solubility space of less than or equal to 20 $(MPa)^{1/2}$ are understood to mean the aliphatic fatty alcohols having at least 6 carbon atoms, the hydrocarbon chain containing no substitution group. As mono-alcohols according to the invention, there may be mentioned oleyl alcohol, decanol, dodecanol, octadecanol and linoleyl alcohol.

Preferably the dispersant is selected from the group consisting of hydrocarbon oils, paraffin oil, liquid petroleum jelly, vison oil, turtle oil, soya bean oil, perhydrosqualene, sweet almond oil, calophyllum oil, palm oil, grapeseed oil, sesame oil, maize oil, parleam oil, arara oil, rapeseed oil, sunflower oil, cottonseed oil, apricot oil, castor oil, avocado oil, jojoba oil, olive oil, cereal germ oil; esters of lanolic acid, esters of oleic acid, esters of lauric acid, esters of stearic acid; isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate, diglyceryl triisostearate, myristic acid, palmitic acid, stearic acid, behenic acid, oleic acid, linoleic acid, linolenic acid, isostearic acid; cetanol, stearyl alcohol, oleyl alcohol, linoleyl or linolenyl alcohol, isostearyl alcohol or octyl dodecanol; silicone oils, polydimethylsiloxane, phenylated polydimethylsiloxane, polymethylphenylsiloxanes, phenyl trimethicones, phenyl trimethicones substituted with fluorinated aliphatic and/or aromatic groups, phenyl trimethicones substituted with functional groups such as hydroxyl, thiol and/or amine groups; polysiloxanes modified with fatty acids, fatty alcohols or polyoxyalkylenes; fluorinated silicones, perfluorinated oils, vegetable oils, sunflower oil, sesame oil, rapeseed oil, the esters long-chain acids or alcohols having the formula RCOOR' in which R represents the residue of a higher fatty acid containing from 7 to 19 carbon atoms and R' represents a hydrocarbon chain containing from 3 to 20 carbon atoms, hydrogenated polyisobutylene, isododecane, volatile isoparaffins, oleyl alcohol, decanol, dodecanol, octadecanol and linoleyl alcohol.

The choice of the non-aqueous medium is made by persons skilled in the art as a function of the nature of the monomers constituting the polymer and/or of the nature of the stabilizer, as indicated below. In particular, it is possible to use a polar or weakly polar oils such as vegetable oils of the long carbon chain-containing triglyceride type (apricot oil, jojoba oil) or the long carbon chain-containing esters such as octyldodecyl neopentanoate, the alkanes such as parleam oil, and the silicone oils. Furthermore, the total liquid lipophilic or fatty phase in which the polymer is dispersed may represent from 30% to 98% of the total weight of the composition and preferably from 30 to 75%. These ranges for the total liquid lipophilic or fatty phase include all specific values and sub-ranges therebetween, including 35, 40, 45, 50, 60, 70, 80, 85, 90 and 95% of the total weight of the composition. The nonvolatile part represents at least 0.5% and in practice from 1 to 30% of the total weight of the composition. These ranges for the nonvolatile part include all specific values and subranges therebetween, including 2, 3, 5, 10, 15, 20 and 25% of the total weight of the composition.

The personal care applications where the compositions of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients or active ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, solid or liquid silicone resins, silicone quats, organic oils, waxes, film formers, thickening agents such as, for example, fumed silica or hydrated silica, particulate fillers, such as for example, talc, kaolin, starch, modified starch, mica, nylon, polymethylsilsequioxane, clays, such as, for example, bentonite and organo-modified clays.

Suitable personal care compositions are made by combining, in a manner known in the art, such as, for example, by mixing, one or more of the above components with the siloxane copolymer network or precursors thereto, preferably in the form of the silicone compositions of the present invention. Thus the entrapped, occluded or encapsulated materials may be incorporated into the silicone network at any point in the preparation of the cosmetic compositions of the present invention provided they do not interfere with the preparation of the silicone gel or siloxane copolymer network. Suitable personal care compositions may be in the form of a single phase or in the form of an emulsion, including but not limited to oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

The compositions of the present invention may be utilized as prepared or as one or more components in emulsions. As is generally known, emulsions comprise at least two immiscible phases one of which is continuous and the other which is discontinuous. Further emulsions may be liquids with varying viscosities comprising solids. Additionally the particle size of the emulsions may render them microemulsions and when sufficiently small such microemulsions may be transparent. Further it is also possible to prepare emulsions of emulsions and these are generally known as multiple emulsions.

These primary types of emulsions may be:
- aqueous emulsions where the continuous phase comprises water and the discontinuous phase comprises the polyether siloxane copolymer network of the present invention;
- aqueous emulsions where the continuous phase comprises the polyether siloxane copolymer network of the present invention and the discontinuous phase comprises water;
- non-aqueous emulsions where the discontinuous phase comprises a non-aqueous hydroxylic solvent and the continuous phase comprises the polyether siloxane copolymer network of the present invention; and
- non-aqueous emulsions where the continuous phase comprises a non-aqueous hydroxylic organic solvent and the discontinuous phase comprises the polyether siloxane copolymer network of the present invention.

Non-aqueous emulsions comprising a silicone phase are described in U.S. Pat. Nos. 6,060,546 and 6,271,295 the disclosures of which are herewith and hereby specifically incorporated by reference.

As used herein the term "non-aqueous hydroxylic organic compound" means hydroxyl containing organic compounds as exemplified by but not limited to alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase (that may or may not contain so-called non-intended water), a hydrous mixture comprising the silicone phase, a water-in-oil emulsion, an oil-in-water emulsion, or either of the two non-aqueous emulsions or variations thereon, the resulting material is usually a high viscosity cream with good feel characteristics, and high absorbance of volatile solvent. It is capable of being blended into formulations for hair care, skin care, antiperspirants, sunscreens, cosmetics, color cosmetics, insect repellants, vitamin and hormone carriers, fragrance carriers and the like.

Colored materials suitable for use in the compositions of the present invention vary according to the laws of the country where the compositions are being sold because they involve topical application to human beings. However, even though categorized by the suitability for use in the United States (US) or in the European Union (EU) the term colored materials includes all the colored materials in the following lists, lists A through D inclusive and all possible sub-combinations thereof:

List A. Certified Organic Colors Listed for Cosmetic Uses in the U.S. and EU:

FD&C blue no. 1, FD&C green no. 3, FD&C red no. 4, FD&C red no. 40, FD&C yellow no. 5, FD&C yellow no. 6, D&C blue no. 4, D&C brown no. 1, D&C green no. 5, D&C green no. 6, D&C green no. 8, D&C orange no. 4, D&C orange no. 5, D&C orange no. 10, D&C orange no. 11, D&C red no. 6, D&C red no. 7, D&C red no. 17, D&C red no. 21, D&C red no. 22, D&C red no. 27, D&C red no. 28, D&C red no. 30, D&C red no. 31, D&C red no. 33, D&C red no. 34, D&C red no. 36, D&C violet no. 2, D&C yellow no. 7, D&C yellow no. 8, D&C yellow no. 10, D&C yellow no. 11, Ext. D&C violet no. 2, and Ext. D&C yellow no. 7.

List B. Inorganic Colors Listed for Cosmetic Uses in the U.S. and EU:

Iron oxide (red, yellow, black), Titanium dioxide, Zinc oxide, Ultramarine, Bismuth oxychloride, Chromium oxide green, Chromium hydroxide green, Ferric ferrocyanide, Manganese violet, and Guanine List C. Additional only EU-Approved Colors List for Cosmetic Uses:

Acid green no. 1, Pigment yellow no. 1, Pigment yellow no. 3, Solvent red no. 3, Solvent red no. 1, Pigment red no. 112, Pigment red no. 5, Acid orange no. 6, Acid red no. 14, Pigment red no. 68, Pigment red no. 48, Acid red no. 27 & Al lake, Acid red no. 18, Acid black no. 1, Pigment yellow no. 13, Solvent yellow no. 29, Acid red no. 73, Brilliant black no. 1, Acid blue no. 1, Acid blue no. 3, Basic violet no. 14, Basic blue no. 26, Acid green no. 50, Acid red no. 52, Acid violet no. 9, Acid red no. 51, Pigment violet no. 23, Pigment red no. 83, Acid blue no. 62, Acid blue no. 74, Pigment violet no. 19, Pigment blue no. 15, Direct blue no. 86, Pigment green no. 7, Bentonite, Barium sulfate, Calcium sulfate, Carbon black, Iron oxide (orange), Magnesium carbonate, Lactoflavin, Capsanthin, capsorubin, Beetroot red, Anthocyanins, Aluminum stearate, Zinc stearate, Magnesium stearate, Calcium stearate, Bromothymol blue, Bromocresol green, Acid red, Color Index (CI) 195, CI 18736, CI 18820, CI 18965, CI 20040, CI 21108, CI 24790, CI 27755, CI 40215, CI 40820, CT 40825, CI 40850, CI 42080, CI 42090, CI 42100, CI 42170, CI 42520, CI 42735, CI 45220, CI 45396, CI 45405, CI 50325, CI 50420, CI 60724, CI 61585, CI 69800, CI 69825, CI 71105, CI 73000, CI 73385, CI 73915, CI 74100, CI 75100, CI 75125, CI 75135, CI 75300, CI 77002, CI 77015, CI 77220, CI 77267, CI 77268:1, CI 77346, CI 77480, and CI 77745

List D. Other Colors List for Cosmetic Uses:

Beta carotene, Annatto, Caramel, Carmine, Chlorophyllin-copper complex, Henna, Aluminum powder, Bronze or copper powder, Silver, Mica, and Titanated mica.

EXPERIMENTAL

Example 1

Gel 1 (Silicone Gel II) was prepared as follows: 260 g of a silicone polymer with the average structure $HMe_2SiO(Me_2SiO)_{133}(MeHSiO)_{2.5}SiMe_2H$ was mixed with 8.5 g vinyl cyclohexeneoxide, 21.7 g C30+ Alpha Olefin (Gulftene C30+ from Chevron), 0.075 g of a solution of a platinum divinyl tetramethysiloxne complex in excess divinyl tetramethyldisiloxane (Karstedt's Catalyst), and 690 g of decamethylcyclopentasiloxane. The result was heated to 90-90° C. for 45 minutes. At this point a blend of 8.8 g of a polymer with approximate structure $Me_3SiO(MeHSiO)_{50}SiMe_3$ and 10.0 g decamethylcyclopentasiloxane was added. Heating was continued another 5.5 hours after which 10 g of a mixture of C16-18 alpha olefins was added. After another 30 minutes at temperature the batch was cooled and the resulting gel isolated.

Example 2

Gel 2 (Silicone Gel I) was prepared as follows: 250 parts of organopolysiloxane with the average structure $CH_2=CH-Me_2SiO(Me_2SiO)_{800}SiMe_2-CH=CH_2$, 1.11 parts of $(M^H_2Q)_4$, 750 parts of decamethylcyclo-pentasiloxane were mixed at room temperature for 1 hour. Then 0.045 parts of Karstedt's catalyst was added. Gelation occurred within 15 minutes at room temperature. The reaction was then heated and maintained at 100° C. for 2 h. The reaction was then cooled down to room temperature to yield a powdered silicone gel.

Example 3

Gel 3 (Silicone Gel VI) was prepared as follows: 244.7 g of organopolysiloxane with the average structure $Me_3SiO(Me_2SiO)_{20}(MeHSiO)_3SiMe_3$, 17.2 g of 1,5-hexadiene, 753.4 g of decamethylcyclopentasiloxane and 0.1 g of Karstedt's catalyst were mixed at room temperature. Gelation occurred within 1 hour. The reaction was then heated and maintained at 100° C. for 1 h. The reaction was then cooled down to room temperature to yield a powdered silicone gel.

Example 4

Gel 4 (Silicone Gel IV) was prepared as follows: 98.25 g of organopolysiloxane with the average structure $Me_3SiO(Me_2SiO)_{20}(MeHSiO)_3SiMe_3$, 151.6 g of organopolysiloxane with the average structure $CH_2=CH-Me_2SiO(Me_2SiO)_{20}SiMe_2-CH=CH_2$, 750 g of decamethylcyclopentasiloxane were mixed at room temperature for 1 hour. Then 0.075 g of Karstedt's catalyst in 100 g of decamethylcyclopentasiloxane was added. Gelation occurred within 30 minutes at room temperature. The reaction was then heated and maintained at 100° C. for 2 h. The reaction was then cooled down to room temperature to yield a powdered silicone gel.

Example 5

Gel 5 (Silicone Gel II) was prepared as follows: 260 g of a silicone polymer with the average structure $HMe_2SiO(Me_2SiO)_{133}(MeHSiO)_{25}SiMe_2H$ was mixed with 8.5 g vinyl cyclohexeneoxide, 21.7 g C30+ Alpha Olefin (Gulftene C30+ from Chevron), 0.075 g Karstedt's Catalyst, and 687 g of isododecane. The result was heated to 90-90° C. for 45 minutes. At this point a blend of 10 g of a polymer with approximate structure $Me_3SiO(MeHSiO)_{50}SiMe_3$ and 10.0 g isododecane was added. Heating was continued another 5.5 hours after which 10 g of a mixture of C16-18 alpha olefins was added. After another 30 minutes at temperature the batch was cooled and the resulting gel isolated.

Example 6

115.4 g of octyl salicylate, 115.4 g of benzophenone-3 and 269.2 g of octyl methoxy cinnamate were mixed and warmed to 40° C. for 45 minutes. This mixture was then filtered to remove undissolved particles. 400 g of this filtrate was then mixed with 600 g of isododecane. To this mixture was added 1000 g of Gel 1. This was then mixed well to yield a slurry. 1 h after preparation of this slurry, the gel was processed by passing through a Gaulin homogenizer at 8000 psi pressure to yield a cream that had a viscosity of 135,000 cps (at 25° C.).

Example 7

136.5 g of isododecane was mixed with 85 g of octyl salicylate. To this mixture was added 350 g of Gel 3. This was then mixed well to yield a slurry. This slurry was processed by passing through a Gaulin homogenizer at 8000 psi pressure to yield a cream that had a viscosity of 65,000 cps (at 25° C.).

Example 8

To 246 g of decamethylcyclopentasiloxane, was added 50 g of silicone quat TP3877 (available from GE Bayer Silicones). To this mixture was added 204 g of a Gel 1. This was then mixed well to yield a slurry. This slurry was processed by passing through a Gaulin homogenizer at 8000 psi pressure to yield a cream that had a viscosity of 242,500 cps (at 25° C.).

Example 9

To 61.6 of silicone copolyol SF1540 (available from GE Silicones) was added 125.9 g of decamethylcyclopentasiloxane. To this mixture was added 312.5 g of a Gel 4. This was then mixed well to yield a slurry. This slurry was processed by passing through a Gaulin homogenizer at 8000 psi pressure to yield a cream that had a viscosity of 292,500 cps (at 25° C.).

Example 10

To 100 g of Silicone based Aloe extract (CLX 7335, Supplied by Collaborative Labs) was added 240 g of decamethylcyclopentasiloxane. To this mixture was added 140 g of Gel 2. This was then mixed well to yield a slurry, which was processed by passing through a Gaulin homogenizer three times at 8000 psi pressure to yield a cream that had a viscosity of 227,500 cps (at 25° C.).

Example 11

To 104 g of Silicone based Green Tea Extract (Silox GT, Supplied by Collaborative Labs) was added 192 g of decamethylcyclopentasiloxane. To this mixture was added 204 g of Gel 1. This was then mixed well to yield a slurry. This slurry was processed by passing through a Gaulin homogenizer at 8000 psi pressure to yield a cream that had a viscosity of 142,500 cps (at 25° C.).

Example 12

To 25 g of methylsesquioxane powder Tospearl 2000B (available from GE Toshiba Silicones) was added 288.5 of Gel 3 and 186.5 g of decamethylcyclopentasiloxane. This was then mixed well to yield a slurry. This slurry was processed by passing through a Gaulin homogenizer at 8000 psi pressure to yield a cream that had a viscosity of 87,500 cps (at 25° C.).

Example 13

50 g of solid silicone resin SR 1000 (available from GE Silicones) was dissolved in 465 g isododecane. Next, 485 g of Gel 5 was added. After thorough mixing the slurry was passed through a Gaulin homogenizer one time at 8000 psi to give a cream with a viscosity of 143,500 cps (at 25° C.).

Example 14

102 g of a 50% solution of a silicone copolyol in decamethylcyclopentasiloxane was mixed with an additional 491 g of decamethylcyclopentasiloxane. At this point 407 g of Gel 1 from above was blended in and the resulting mixture was passed through a Gaulin homogenizer at 8000 psi. This gave a cream with a viscosity of 115,000 cps (at 25° C.).

These examples are to be construed as exemplary in nature only and are not intended in any way to limit the appended claims. While these examples have shown one particular order of adding the active ingredients and various components to produce the cosmetic compositions of the present invention, it is contemplated that other orders of addition may produce different benefits. The order of addition explicitly taught herein is not to be interpreted as the exclusive manner of producing the mixtures that represent the compositions that can be produced by the techniques of the present invention. Such different orders of addition could be for example adding active ingredients, e.g. personal care ingredients, prior to homogenization or particle size reduction of the copolymer network or alternatively adding such active ingredients after homogenization. It is contemplated that a person having ordinary skill in the art would be able to produce obvious variations of the subject matter and disclosures herein contained that would be by reason of such ordinary skill within the literal or equitable scope of the appended claims.

Having described the invention that which is claimed is:

1. A method for preparing a cosmetic composition comprising:
   (a) preparing a silicone gel in the presence of a pigment said gel selected from the group of silicone gels consisting of:
      (i) a gel formed from a silicone and a hydrosilylation compatible solvent wherein said silicone is prepared by the hydrosilylation of a linear alkenyl polyorganosiloxane and a hydride resin;
      (ii) a gel formed as a reaction product of an epoxy functional hydrido-siloxane said reaction product being formed in an epoxy-gel formation compatible solvent;
      (iii) a gel formed from a silicone and a hydrosilylation compatible solvent wherein said silicone is prepared by the hydrosilylation of a linear hydrogen organopolysiloxane having two or more hydride functionalities per molecule and an α, ω reactive organic molecule possessing two or more reactive functionalities per molecule; and
      (iv) a gel formed as a reaction product of a vinyl functional hydrido-siloxane in a hydrosilylation compatible solvent;
   wherein said cosmetic composition comprises a pigment selected from the group consisting of FD&C blue no. 1, FD&C green no. 3, FD&C red no. 4, FD&C red no. 40, FD&C yellow no. 5, FF&C yellow no. 6, D&C blue no. 4, D&C brown no. 1, D&C green no. 5, D&C green no. 6, D&C green no. 8, D&C orange no. 4, D&C orange no. 5, D&C orange no. 10, D&C orange no. 11, D&C red no. 6, D&C red no. 7, D&C red no. 17, D&C red no. 21, D&C red no. 22, D&C red no. 27, D&C red no. 28, D&C red no. 30, D&C red no. 31, D&C red no. 33, D&C red no. 34, D&C red no. 36, D&C violet no. 2, D&C yellow no. 7, D&C yellow no. 8, D&C yellow no. 10, D&C yellow no. 11, Ext. D&C violet no. 2, Ext. D&C yellow no. 7, Iron oxide (red, yellow, black), Titanium dioxide, Zinc oxide, Ultramarine, Bismuth oxychioride, Chromium oxide green, Chromium hydroxide green, Ferric ferrocyanide, Manganese violet, Guanine, Acid green no. 1, Pigment yellow no. 1, Pigment yellow no. 3, Solvent red no. 3, Solvent red no. 1, Pigment red no. 112, Pigment red no. 5, Acid orange no. 6, Acid red no. 14, Pigment red no. 68, Pigment red no. 48, Acid red no. 27 & Al lake, Acid red no. 18, Acid black no. 1, Pigment yellow no. 13, Solvent yellow no. 29, Acid red no. 73, Brilliant black no. 1, Acid blue no. 1, Acid blue no. 3, Basic violet no. 14, Basic blue no. 26, Acid green no. 50, Acid red no. 52, Acid violet no. 9, Acid red no. 51, Pigment violet no. 23, Pigment red no. 83, Acid blue no. 62, Acid blue no. 74, Pigment violet no. 19, Pigment blue no. 15, Direct blue no. 86, Pigment green no. 7, Bentonite, Barium sulfate, Calcium sulfate, Carbon black, Iron oxide (orange), Magnesium carbonate, Lactoflavin, Capsanthin, capsorubin, Beetroot red, Anthocyanins, Aluminum stearate, Zinc stearate, Magnesium stearate, Calcium stearate, Bromothymol blue, Bromocresol green, Acid red, Color Index (CI) 195, CI 18736, CI 18820, CI 18965, CI 20040, CI 21108, CI 24790, CI 27755, CI 40215, CI 40820, CI 40825, CI 40850, CI 42080, CI 42090, CI 42100, CI 42170, CI 42520, CI 42735, CI 45220, CI 45396, CI 45405, CI 50325, CI 50420, CI 60724, CI 61585, CI 69800, CI 69825, CI 71105, CI 73000, CI 73385, CI 73915, CI 74100, CL 75100, CI 75125, CI 75135, CI 75300, CL 77002, CI 77015, CI 77220, CI 77267, CI 77268:1, CI 77346, CI 77480, CI 77745, Beta carotene, Annatto, Caramel, Carmine, Chlorophyllin-copper complex, Henna;

(b) dispersing the silicone gel in a dispersant medium selected from the group consisting of hydrocarbon oils, paraffin oil, liquid petroleum jelly, vison oil, turtle oil, soya bean oil, perhydrosqualene, sweet almond oil, calophyllum oil, palm oil, grapeseed oil, sesame oil, maize oil, parleam oil, arara oil, rapeseed oil, sunflower oil, cottonseed oil, apricot oil, castor oil, avocado oil, jojoba oil, olive oil, cereal germ oil; esters of lanolic acid, esters of oleic acid, esters of lauric acid, esters of stearic acid; isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethyihexyl succinate, diisostearyl malate, glyceryl triisostearate, diglyceryl triisostearate, myristic acid, palmitic acid, stearic acid, behenic acid, oleic acid, linoleic acid, linolenic acid, isostearic acid; cetanol, stearyl alcohol, oleyl alcohol, linoleyl or linolenyl alcohol, isostearyl alcohol or octyl dodecanol; silicone oils, polydimethylsiloxane, phenylated polydimethylsiloxane, polymethyiphenylsiloxanes, phenyl trimethicones, phenyl trimethicones substituted with fluorinated aliphatic and/or aromatic groups, phenyl trimethicones substituted with functional groups such as hydroxyl, thiol and/or amine groups; polysiloxanes modified with fatty acids, fatty alcohols or polyoxyalkylenes; fluorinated silicones, perfluorinated oils, vegetable oils, sunflower oil, sesame oil, rapeseed oil, the esters long-chain acids or alcohols having the formula RCOOR' in which R represents the residue of a higher fatty acid containing from 7 to 19 carbon atoms and R' represents a hydrocarbon chain containing from 3 to 20 carbon atoms, hydrogenated polyisobutylene, isododecane, volatile isoparaffins, olcyl alcohol, decanol, dodecanol, octadecanol and linoleyl alcohol; and (c) homogenizing said silicone gel in said dispersant medium.

2. The method of claim 1 wherein the cosmetic is selected from the group consisting of lipsticks, foundations, face powders, eye liners, eye shadows, blushes, makeup, and mascara.

3. The method of claim 1 wherein the silicone gel is a gel formed from a silicone and a hydrosilylation compatible solvent wherein said silicone is prepared by the hydrosilylation of a linear alkenyl polyorganosiloxane and a hydride resin.

4. The method of claim 1 wherein the silicone gel is a gel formed as a reaction product of an epoxy functional hydridosiloxane said reaction product being formed in an epoxy-get formation compatible solvent.

5. The method of claim 1 wherein the silicone gel is a gel formed from a silicone and a hydrosilylation compatible solvent wherein said silicone is prepared by the hydrosilylation of a linear hydrogen organopolysiloxane having two or more hydride functionalities per molecule and an $\alpha, \omega$ reactive organic molecule possessing two or more reactive functionalities per molecule.

6. The method of claim 1 wherein the silicone gel is a gel formed as a reaction product of a vinyl functional hydridosiloxane in a hydrosilylation compatible solvent.

7. A method for preparing a cosmetic composition comprising:
  (a) using hydrosilylation in the presence of a pigment to prepare a silicone gel comprising an entrapped or encapsulated pigment selected from the group of silicone gels consisting of:
    (i) a gel formed from a silicone and a hydrosilylation compatible solvent wherein said silicone is prepared by the hydrosilylation of a Linear alkenyl polyorganosiloxane and a hydride resin;
    (ii) gel formed from a silicone and hydrosilylation compatible solvent wherein said silicone is prepared by the hydrosilylation of a hydrogen polyorganosiloxane resin and an alkenyl polyorganosiloxane resin;
    (iii) a gel formed from a silicone and a hydrosilylation compatible solvent wherein said silicone is prepared by the hydrosilylation of a linear hydrogen organopolysiloxane having two or more hydride functionalities per molecule and an $\alpha, \omega$ reactive organic molecule possessing two or more reactive functionalities per molecule; and
    (iv) a gel formed as a reaction product of a vinyl functional hydrido-siloxane in a hydrosilylation compatible solvent;
wherein said cosmetic composition comprises a pigment selected from the group consisting of FD&C blue no. 1, FD&C green no. 3, FD&C red no. 4, FD&C red no. 40, FD&C yellow no. 5, FF&C yellow no. 6, D&C blue no. 4, D&C brown no. 1, D&C green no. 5, D&C green no. 6, D&C green no. 8, D&C orange no. 4, D&C orange no. 5, D&C orange no. 10, D&C orange no. 11, D&C red no. 6, D&C red no. 7, D&C red no. 17, D&C red no. 21, D&C red no. 22, D&C red no. 27, D&C red no. 28, D&C red no. 30, D&C red no. 31, D&C red no. 33, D&C red no. 34, D&C red no. 36, D&C violet no. 2, D&C yellow no. 7, D&C yellow no. 8, D&C yellow no. 10, D&C yellow no. 11, Ext. D&C violet no. 2, Ext. D&C yellow no. 7, Iron oxide (red, yellow, black), Titanium dioxide, Zinc oxide, Ultramarine, Bismuth oxychloride, Chromium oxide green, Chromium hydroxide green, Ferric ferrocyanide, Manganese violet, Guanine, Acid green no. 1, Pigment yellow no.1, Pigment yellow no. 3, Solvent red no. 3, Solvent red no. 1, Pigment red no. 112, Pigment red no. 5, Acid orange no. 6, Acid red no. 14, Pigment red no. 68, Pigment red no. 48, Acid red no. 27 & Al lake, Acid red no. 18, Acid black no. 1, Pigment yellow no. 13, Solvent yellow no. 29, Acid red no. 73, Brilliant black no. 1, Acid blue no. 1, Acid blue no. 3, Basic violet no. 14, Basic blue no. 26, Acid green no. 50, Acid red no. 52, Acid violet no. 9, Acid red no. 51, Pigment violet no. 23, Pigment red no. 83, Acid blue no. 62, Acid blue no. 74, Pigment violet no. 19, Pigment blue no. 15, Direct blue no. 86, Pigment green no. 7, Bentonite, Barium sulfate, Calcium sulfate, Carbon black, Iron oxide (orange), Magnesium carbonate, Lactoflavin, Capsanthin, capsorubin, Beetroot red, Anthocyanins, Aluminum stearate, Zinc stearate, Magnesium stearate, Calcium stearate, Bromothymol blue, Bromocresol green, Acid red, Color Index (CI) 195, CI 18736, CI 18820, CI 18965, CI 20040, CI 21108, CI 24790, CI 27755, CI 40215, CI 40820, CI 40825, CI 40850, CI 42080, CI 42090, CI 42100, CI 42170, CI 42520, CI 42735, CI 45220, CI 45396, CI 45405, CI 50325, CI 50420, CI 60724, CL 61585, CI 69800, CI 69825, CI 71105, CI 73000, CI 73385, CI 73915, CI 74100, CI 75100, CI 75125, CI 75135, CI 75300, CI 77002, CI 77015, CI 77220, CI 77267, CI 77268:1, CI 77346, CI 77480, CI 77745, Beta carotene, Annatto, Caramel, Carmine, Chlorophyllin-copper complex, Henna;

(b) dispersing the silicone gel in a dispersant medium selected from the group consisting of hydrocarbon oils, paraffin oil, liquid petroleum jelly, vison oil, turtle oil, soya bean oil, perhydrosqualene, sweet almond oil, calophyllum oil, palm oil, grape seed oil, sesame oil, maize oil, parleam oil, arara oil, rapeseed oil, sunflower oil, cottonseed oil, apricot oil, castor oil, avocado oil, jojoba oil, olive oil, cereal germ oil; esters of Lanolic acid, esters of oleic acid, esters of lauric acid, esters of stearic acid; isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl tuiisostearate, diglyceryl triisostearate, myristic acid, palmitic acid, stearic acid, behenic acid, oleic acid, linoleic acid, linolenic acid, isostearic acid; cetanol, stearyl alcohol, oleyl alcohol, linoleyl or linolenyl alcohol, isostearyl alcohol or octyl dodecanol; silicone oils, polydimethylsitoxane, phenylated polydimethylsiloxane, polymethyiphenylsiloxanes, phenyl trimethicones, phenyl trimethicones substituted with fluorinated aliphatic and/or aromatic groups, phenyl trimethicones substituted with functional groups such as hydroxyl, thiol and/or amine groups; polysiloxanes modified with fatty acids, fatty alcohols or polyoxyalkylenes; fluorinated silicones, perfluorinated oils, vegetable oils, sunflower oil, sesame oil, rapeseed oil, the esters long-chain acids or alcohols having the formula RCOOR' in which R represents the residue of a higher fatty acid containing from 7 to 19 carbon atoms and R' represents a hydrocarbon chain containing from 3 to 20 carbon atoms, hydrogenated polyisobutylene, isododecane, volatile isoparaffins, oleyl alcohol, decanol, dodecanol, octadecanol and linoleyl alcohol; and (c) homogenizing said silicone gel in said dispersant medium; and (d) adding thereto a personal care ingredient.

8. The method of claim 7 wherein the cosmetic is selected from the group consisting of lipsticks, foundations, face powders, eye liners, eye shadows, blushes, makeup, and mascara.

9. The method of claim 7 wherein the silicone gel is a gel formed from a silicone and a hydrosilylation compatible solvent wherein said silicone is prepared by the hydrosilylation of a linear alkenyl polyorganosiloxane and a hydride resin.

10. The method of claim 7 wherein the silicone gel is a gel formed from a silicone and a hydrosilylation compatible solvent wherein said silicone is prepared by the hydrosilylation of a linear hydrogen organopolysiloxane having two or more hydride functionalities per molecule and an α, ω reactive organic molecule possessing two or more reactive functionalities per molecule.

11. A method for preparing a cosmetic composition comprising:

(a) preparing a silicone gel in the presence of a pigment thereby comprising an entrapped or encapsulated pigment selected from the group of silicone gels consisting of:

(i) a gel formed from a silicone and a hydrosilylation compatible solvent wherein said silicone is prepared by the hydrosilylation of a linear alkenyl polyorganosiloxane and a hydride resin;

(ii) a gel formed from a silicone and hydrosilylation compatible solvent wherein said silicone is prepared by the hydrosilylation of a hydrogen polyorganosiloxane resin and an alkenyl polyorganosiloxane resin;

(iii) a gel formed from a silicone and a hydrosilylation compatible solvent wherein said silicone is prepared by the hydrosilylation of a linear hydrogen organopolysiloxane having two or more hydride functionalities per molecule and an α, ω reactive organic molecule possessing two or more reactive functionalities per molecule; and (iv) a gel formed as a reaction product of a vinyl functional hydrido-siloxane in a hydrosilylation compatible solvent;

wherein said cosmetic composition comprises a pigment selected from the group consisting of FD&C blue no. 1, FD&C green no. 3, FD&C red no. 4, FD&C red no. 40, FD&C yellow no. 5, FF&C yellow no. 6, D&C blue no. 4, D&C brown no. 1, D&C green no. 5, D&C green no. 6, D&C green no. 8, D&C orange no. 4, D&C orange no. 5, D&C orange no. 10, D&C orange no. 11, D&C red no. 6, D&C red no. 7, D&C red no. 17, D&C red no. 21, D&C red no. 22, D&C red no. 27, D&C red no. 28, D&C red no. 30, D&C red no. 31, D&C red no. 33, D&C red no. 34, D&C red no. 36, D&C violet no. 2, D&C yellow no. 7, D&C yellow no. 8, D&C yellow no. 10, D&C yellow no. 11, Ext. D&C violet no. 2, Ext. D&C yellow no. 7, Iron oxide (red, yellow, black), Titanium dioxide, Zinc oxide, Ultramarine, Bismuth oxychtoride, Chromium oxide green, Chromium hydroxide green, Ferric ferrocyanide, Manganese violet, Guanine, Acid green no. 1, Pigment yellow no. 1, Pigment yellow no. 3, Solvent red no. 3, Solvent red no. 1, Pigment red no. 112, Pigment red no. 5, Acid orange no. 6, Acid red no. 14, Pigment red no. 68, Pigment red no. 48, Acid red no. 27 & Al lake, Acid red no. 18, Acid black no. 1, Pigment yellow no. 13, Solvent yellow no. 29, Acid red no. 73, Brilliant black no. 1, Acid blue no. 1, Acid blue no. 3, Basic violet no. 14, Basic blue no. 26, Acid green no. 50, Acid red no. 52, Acid violet no. 9, Acid red no. 51, Pigment violet no. 23, Pigment red no. 83, Acid blue no. 62, Acid blue no. 74, Pigment violet no. 19, Pigment blue no. 15, Direct blue no. 86, Pigment green no. 7, Bentonite, Barium sulfate, Calcium sulfate, Carbon black, Iron oxide (orange), Magnesium carbonate, Lactoflavin, Capsanthin, capsorubin, Beetroot red, Anthocyaniris, Aluminum stearate, Zinc stearate, Magnesium stearate, Calcium stearate, Bromothymol blue, Bromocresol green, Acid red, Color index (CI) 195, CI 18736, CI 18820, CI 18965, CI 20040, CI 21108, CI 24790, CI 27755, CI 40215, CI 40820, CI 40825, CI 40850, CI 42080, CI 42090, CI 42100, CI 42170, CI 42520, CI 42735, CI 45220, CI 45396, CI 45405, CI 50325, CI 50420, CI 60724, CI 61585, CI 69800, CI 69825, CI 71105, CI 73000, CI 73385, CI 73915, CI 74100, CI 75100, CI 75125, CI 75135, CI 75300, CI 77002, CI 77015, CI 77220, CI 77267, CI 77268:1, CI 77346, CI 77480, CI 77745, Beta carotene, Annatto, Caramel, Carmine, Chiorophyllin-copper complex, Henna;

(b) dispersing the silicone gel in a dispersant medium selected from the group consisting of hydrocarbon oils, paraffin oil, liquid petroleum jelly, vison oil, turtle oil, soya bean oil, perhydrosqualene, sweet almond oil, calophyllum oil, palm oil, grape seed oil, sesame oil, maize oil, parleam oil, arara oil, rapeseed oil, sunflower oil, cottonseed oil, apricot oil, castor oil, avocado oil, jojoba oil, olive oil, cereal germ oil; esters of lanolic acid, esters of oleic acid, esters of lauric acid, esters of stearic acid; isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate, diglyceryl triisostearate, myristic acid, palmitic acid, stearic acid, behenic acid, oleic acid, linoleic acid, linolenic acid, isostearic acid; cetanol, stearyl alcohol, oleyl alcohol, linoleyl or linolenyl alcohol, isostearyl alcohol or octyl dodecanol; silicone oils, polydimethylsiloxane, phenylated polydimethylsiloxane, polymethyiphenylsiloxanes, phenyl trimethicones, phenyl trimethicones substituted with fluorinated aliphatic and/or aromatic groups, phenyl trimethicones substituted with functional groups such as hydroxyl, thiol and/or amine groups; polysiloxanes modified with fatty acids, fatty alcohols or polyoxyalkylenes; fluorinated silicones, perfluorinated oils, vegetable oils, sunflower oil, sesame oil, rapeseed oil, the esters long-chain acids or alcohols having the formula RCOOR' in which R represents the residue of a higher fatty acid containing from 7 to 19 carbon atoms and R' represents a hydrocarbon chain containing from 3 to 20 carbon atoms, hydrogenated polyisobutylene, isododecane, volatile isoparaffins, oleyl alcohol, decanol, dodecanol, octadecanol and linoleyl alcohol;

(c) adding to said silicone gel and said dispersant medium a personal care ingredient; and (d) homogenizing said silicone gel, said dispersant medium and said personal care ingredient.

12. The method of claim 11 wherein the cosmetic is selected from the group consisting of lipsticks, foundations, face powders, eye liners, eye shadows, blushes, makeup, and mascara.

13. The method of claim 11 wherein the silicone gel is a gel formed from a silicone and a hydrosilylation compatible solvent wherein said silicone is prepared by the hydrosilylation of a linear alkenyl polyorganosiloxane and a hydride resin.

14. The method of claim 11 wherein the silicone gel is a gel formed from a silicone and hydrosilylation compatible solvent wherein said silicone is prepared by the hydrosilylation of a hydrogen polyorganosiloxane resin and an alkenyl polyorganosiloxane resin.

15. The method of claim 11 wherein the silicone gel is a gel formed from a silicone and a hydrosilylation compatible solvent wherein said silicone is prepared by the hydrosilylation of a linear hydrogen organopolysiloxane having two or more hydride functionalities per molecule and an α, ω reactive organic molecule possessing two or more reactive functionalities per molecule.

16. The method of claim 11 wherein the silicone gel is a gel formed as a reaction product of a vinyt functional hydrido-siloxane in a hydrositylation compatible solvent.

17. A method for preparing a cosmetic composition comprising:
(a) preparing a silicone gel in the presence of a pigment and personal care ingredients said gel selected from the group of silicone gels consisting of:
(i) a gel formed from a silicone and a hydrosilylation compatible solvent wherein said silicone is prepared by the hydrosilylation of a linear alkenyl polyorganosiloxane and a hydride resin;
(ii) a gel formed as a reaction product of an epoxy functional hydrido-siloxane said reaction product being formed in an epoxy-gel formation compatible solvent;
(iii) a gel formed from a silicone and a hydrosilylation compatible solvent wherein said silicone is prepared by the hydrosilylation of a linear hydrogen organopolysiloxane having two or more hydride functionalities per molecule and an α, ω reactive organic molecule possessing two or more reactive functionalities per molecule; and
(iv) a gel formed as a reaction product of a vinyl functional hydrido-siloxane in a hydrosilylation compatible solvent;

wherein said cosmetic composition comprises a pigment selected from the group consisting of FD&C blue no. 1, FD&C green no. 3, FD&C red no. 4, FD&C red no. 40, FD&C yellow no. 5, FF&C yellow no. 6, D&C blue no. 4, D&C brown no. 1, D&C green no. 5, D&C green no. 6, D&C green no. 8, D&C orange no. 4, D&C orange no. 5, D&C orange no. 10, D&C orange no. 11, D&C red no. 6, D&C red no. 7, D&C red no. 17, D&C red no. 21, D&C red no. 22, D&C red no. 27, D&C red no. 28, D&C red no. 30, D&C red no. 31, D&C red no. 33, D&C red no. 34, D&C red no. 36, D&C violet no. 2, D&C yellow no. 7, D&C yellow no. 8, D&C yellow no. 10, D&C yellow no. 11, Ext. D&C violet no. 2, Ext. D&C yellow no. 7, Iron oxide (red, yellow, black), Titanium dioxide, Zinc oxide, Ultramarine, Bismuth oxychloride, Chromium oxide green, Chromium hydroxide green, Ferric ferrocyanide, Manganese violet, Guanine, Acid green no. 1, Pigment yellow no. 1, Pigment yellow no. 3, Solvent red no. 3, Solvent red no. 1, Pigment red no. 112, Pigment red no. 5, Acid orange no. 6, Acid red no. 14, Pigment red no. 68, Pigment red no. 48, Acid red no. 27 & Al lake, Acid red no. 18, Acid black no. 1, Pigment yellow no. 13, Solvent yellow no. 29, Acid red no. 73, Brilliant black no. 1, Acid blue no. 1, Acid blue no. 3, Basic violet no. 14, Basic blue no. 26, Acid green no. 50, Acid red no. 52, Acid violet no. 9, Acid red no. 51, Pigment violet no. 23, Pigment red no. 83, Acid blue no. 62, Acid blue no. 74, Pigment violet no. 19, Pigment blue no. 15, Direct blue no. 86, Pigment green no. 7, Bentonite, Barium sulfate, Calcium sulfate, Carbon black, Iron oxide (orange), Magnesium carbonate, Lactoflavin, Capsanthin, capsorubin, Beetroot red, Anthocyanins, Aluminum stearate, Zinc stearate, Magnesium stearate, Calcium stearate, Bromothymol blue, Bromocresol green, Acid red, Color Index (CI) 195, CI 18736, CI 18820, CI 18965, CI 20040, CI 21108, CI 24790, CI 27755, CI 40215, CI 40820, CI 40825, CI 40850, CI 42080, CI 42090, CI 42100, CI 42170, Cl 42520, CI 42735, Cl 45220, CI 45396, CI 45405, CI 50325, CI 50420, CI 60724, CI 61585, CI 69800, CI 69825, CI 71105, CI 73000, CI 73385, CI 73915, CI 74100, CI 75100, CI 75125, CI 75135, CI 75300, CI 77002, CI 77015, CI 77220, CI 77267, CI 77268:1, CI 77346, CI 77480, CI 77745, Beta carotene, Annatto, Caramel, Carmine, Chiorophyllin-copper complex, Henna;

(b) dispersing the silicone gel in a dispersant medium selected from the group consisting of hydrocarbon oils, paraffin oil, liquid petroleum jelly, vison oil, turtle oil, soya bean oil, perhydrosqualene, sweet almond oil, calophyllum oil, palm oil, grapeseed oil, sesame oil, maize oil, parleam oil, arara oil, rapeseed oil, sunflower oil, cottonseed oil, apricot oil, castor oil, avocado oil, jojoba oil, olive oil, cereal germ oil; esters of lanolic acid, esters of oleic acid, esters of lauric acid, esters of stearic acid; isopropyl myristate, isopropyl palmitate, butyl stearate, hexyl laurate, diisopropyl adipate, isononyl isononate, 2-ethyihexyl palmitate, 2-hexyldecyl laurate, 2-octyldecyl palmitate, 2-octyldodecyl myristate or lactate, 2-diethylhexyl succinate, diisostearyl malate, glyceryl triisostearate, diglyceryl triisostearate, myristic acid, palmitic acid, stearic acid, behenic acid, oleic acid, linoleic acid, linolenic acid, isostearic acid; cetanol, stearyl alcohol, oleyl alcohol, linoleyl or linolenyl alcohol, isostearyl alcohol or octyl dodecanol; silicone oils, polydimethylsiloxane, phenylated polydimethylsiloxane, polymethylphenylsiloxanes, phenyl trimethicones, phenyl trimethicones substituted with fluorinated aliphatic and/or aromatic groups, phenyl trimethicones substituted with functional groups such as hydroxyl, thiol and/or amine groups; polysiloxanes modified with fatty acids, fatty alcohols or polyoxyalkylenes; fluorinated silicones, perfluorinated oils, vegetable oils, sunflower oil, sesame oil, rapeseed oil, the esters long-chain acids or alcohols having the formula RCOOR' in which R represents the residue of a higher fatty acid containing from 7 to 19 carbon atoms and R' represents a hydrocarbon chain containing from 3 to 20 carbon atoms, hydrogenated polyisobutylene, isododecane, volatile isoparaffins, oleyl alcohol, decanol, dodecanol, octadecanol and linoleyl alcohol; and (c) homogenizing said silicone gel, said dispersant medium and said personal care ingredient.

18. The method of claim 17 wherein the cosmetic is selected from the group consisting of lipsticks, foundations, face powders, eye liners, eye shadows, blushes, makeup, and mascara.

19. The method of claim 17 wherein the silicone gel is a gel formed from a silicone and a hydrosilylation compatible solvent wherein said silicone is prepared by the hydrosilylation of a linear alkenyl polyorganosiloxane and a hydride resin.

20. The method of claim 17 wherein the silicone gel is a gel formed as a reaction product of an epoxy functional hydrido-siloxane said reaction product being formed in an epoxy-gel formation compatible solvent.

21. The method of claim 17 wherein the silicone gel is a gel formed from a silicone and a hydrosilylation compatible solvent wherein said silicone is prepared by the hydrosilylation of a linear hydrogen organopolysiloxane having two or more hydride functionalities per molecule and an $\alpha, \omega$ reactive organic molecule possessing two or more reactive functionalities per molecule.

22. The method of claim 17 wherein the silicone gel is a gel formed as a reaction product of a vinyl functional hydrido-siloxane in a hydrosilylation compatible solvent.

23. The method of claim 19 wherein the personal care ingredient is selected from the group consisting of emollients, moisturizers, humectants, pigments, pearlescent pigment, bismuth oxychioride, titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyois, absorbing agents for ultraviolet radiation, botanical extracts, surfactants, silicone oits, solid or liquid silicone resins, silicone quats, organic oils, waxes, film formers, thickening agents, fumed silica, hydrated silica, particulate fitters, talc, kaolin, starch, modified starch, mica, nylon, polymethylsilsequioxane, clays, bentonite and organo-modified clays.

24. The method of claim 20 wherein the personal care ingredient is selected from the group consisting of emollients, moisturizers, humectants, pigments, pearlescent pigment, bismuth oxychloride, titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surf actants, silicone oils, solid or liquid silicone resins, silicone quats, organic oils, waxes, film formers, thickening agents, fumed silica, hydrated silica, particulate fillers, talc, kaolin, starch, modified starch, mica, nylon, polymethylsilsequioxane, clays, bentonite and organo-modified clays.

25. The method of claim 21 wherein the personal care ingredient is selected from the group consisting of emollients, moisturizers, humectants, pigments, pearlescent pigment, bismuth oxychioride, titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, solid or liquid silicone resins, silicone quats, organic oils, waxes, film formers, thickening agents, fumed silica, hydrated silica, particulate fillers, talc, kaolin, starch, modified starch, mica, nylon, polymethylsilsequioxane, clays, bentonite and organo-modified clays.

26. The method of claim 22 wherein the personal care ingredient is selected from the group consisting of emollients, moisturizers, humectants, pigments, pearlescent pigment, bismuth oxychloride, titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surf actants, silicone oils, solid or liquid silicone resins, silicone quats, organic oils, waxes, film formers, thickening agents, fumed silica, hydrated silica, particulate fillers, talc, kaolin, starch, modified starch, mica, nylon, polymethylsilsequioxane, clays, bentonite and organo-modified clays.

\* \* \* \* \*